(12) United States Patent
Chang et al.

(10) Patent No.: US 8,879,852 B2
(45) Date of Patent: Nov. 4, 2014

(54) NON-CONTRAST-ENHANCED 4D MRA USING COMPRESSED SENSING RECONSTRUCTION

(75) Inventors: Ti-chiun Chang, Princeton Junction, NJ (US); Mariappan S. Nadar, Plainsboro, NJ (US); Jens Gühring, Erlangen (DE); Michael Zenge, Nürnberg (DE); Kai Tobias Block, New York, NY (US); Peter Schmitt, Weisendorf (DE); Edgar Mueller, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/284,143

(22) Filed: Oct. 28, 2011

(65) Prior Publication Data

US 2013/0121550 A1   May 16, 2013

Related U.S. Application Data

(60) Provisional application No. 61/412,084, filed on Nov. 10, 2010.

(51) Int. Cl.
| | |
|---|---|
| G06K 9/00 | (2006.01) |
| G01R 33/561 | (2006.01) |
| A61B 5/055 | (2006.01) |
| G06T 11/00 | (2006.01) |
| G01R 33/563 | (2006.01) |
| G01R 33/565 | (2006.01) |

(52) U.S. Cl.
CPC ............ *G06T 11/003* (2013.01); *G01R 33/561* (2013.01); *G01R 33/5635* (2013.01); *G01R 33/56545* (2013.01); *A61B 5/055* (2013.01)
USPC ........................................................ 382/206

(58) Field of Classification Search
None
See application file for complete search history.

(56) References Cited

U.S. PATENT DOCUMENTS

| | | | | |
|---|---|---|---|---|
| 2005/0174113 | A1* | 8/2005 | Tsao et al. | 324/307 |
| 2007/0195932 | A1* | 8/2007 | Nakaura et al. | 378/98.12 |
| 2008/0009705 | A1* | 1/2008 | Furudate | 600/410 |
| 2008/0247503 | A1* | 10/2008 | Lauritsch et al. | 378/4 |
| 2009/0080749 | A1* | 3/2009 | Visser et al. | 382/131 |
| 2011/0071382 | A1* | 3/2011 | Miyazaki et al. | 600/413 |
| 2011/0090309 | A1* | 4/2011 | Suzuki et al. | 348/43 |
| 2011/0133094 | A1* | 6/2011 | Seppi et al. | 250/367 |
| 2011/0148413 | A1* | 6/2011 | Miyazaki et al. | 324/309 |

(Continued)

OTHER PUBLICATIONS

T-C. Chang, L. He, T. Fang; "MR Image Reconstruction form Sparse Radial Samples Using Bregman Iteration", 2006, Proc. International Society Mag. Reson. Med. 14.*

(Continued)

*Primary Examiner* — Nirav G Patel
*Assistant Examiner* — Oneal R Mistry

(57) ABSTRACT

A reconstructed image is rendered of a patient by a processor from a set of undersampled MRI data by first subtracting two repetitions of the acquired data in k-space to create a third dataset. The processor reconstructs the image by minimizing an objective function under a constraint related to the third dataset, wherein the objective function includes applying a Karhunen-Loeve Transform (KLT) to a temporal dimension of data. The objective function under the constraint is expressed as arg $\min_f \{\|\phi(f)\|_1$ subject to $\|Af-y\|_2 \le \epsilon\}$. The reconstructed image is an angiogram which may be a 4D angiogram. The angiogram is used to diagnose a vascular disease.

14 Claims, 8 Drawing Sheets

(56) References Cited

U.S. PATENT DOCUMENTS

2012/0019244 A1* 1/2012 Chen et al. .................... 324/309
2012/0095326 A1* 4/2012 Miyazaki ...................... 600/413
2012/0112751 A1* 5/2012 Littmann et al. ............. 324/322

OTHER PUBLICATIONS

Yu Ding, Yiu-Cho, Subha V. Raman, and Orlando Simonetti, "Application of the Karhunen-Loeve transform temporal image filter to reduce noise in real-time cardiac cine MRI"; 2009, Phys. Med. Biol. 54.*

H. Jung, K. Sung, K. Nayak, E. Kim, J. Chul Ye. "K-T Focuss: A Gneral Compressed Sensing Framework for High Resolution Dynamic MRI" Magnetic Resonance in Medicine, 61:103, Wiley-Liss. 2008, hereinafter Jung.*

Chang et al. "MR Image Reconstruction from Sparse Radial Samples Using Bregman Iteration" Proc. Intl. Soc. Mag. Reson. Med.,14 (2006), hereinafter Chang.*

* cited by examiner

Compressed sensing (CS) framework 401

$$\arg\min_{f} \ \| \varphi(\mathbf{f}) \|_1, \quad \text{s.t.} \ \| A\mathbf{f} - y \|_2 < \varepsilon \qquad (1)$$

f : series of images to be reconstructed
$\varphi$ : sparsifying transform
$A$ : Encoding matrix
$y$ : measurement data
$\varepsilon$ : data fidelity parameter

FIG. 4

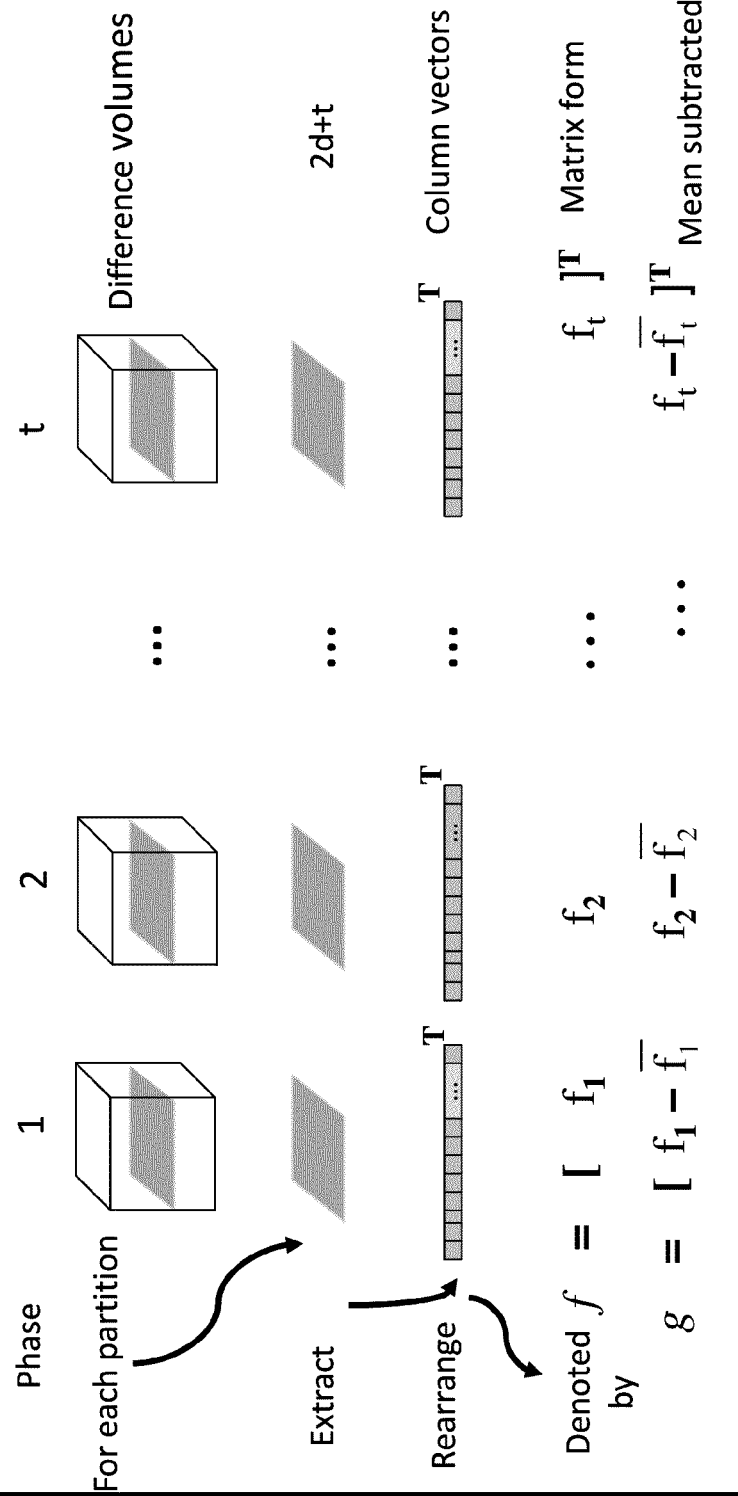

US 8,879,852 B2

NON-CONTRAST-ENHANCED 4D MRA USING COMPRESSED SENSING RECONSTRUCTION

STATEMENT OF RELATED CASES

This application claims the benefit of U.S. Provisional Application No. 61/412,084 filed Nov. 10, 2010, which is incorporated herein by reference.

BACKGROUND OF THE INVENTION

The present invention relates generally to medical imaging, and more particularly to iterative reconstruction of images.

In recent years, non-contrast magnetic resonance angiography (NCE MRA) has been an emerging tool in the diagnosis of degenerative vascular disease. Desired improvements include a reduction of the total scan time to reduce the impact of unintentional motion as well as an increase of the spatial and/or temporal resolution. Thus, the compressed sensing (CS) technique, which aims at reconstructing high quality signal from largely undersampled acquisitions, is a natural fit to further enhance time-resolved NCE-MRA applications and to generate 4D angiograms.

Magnetic Resonance Imaging (MRI) has become a well-established medical diagnostic tool for imaging structures within the body of a patient. Image quality may be characterized by a host of parameters, including resolution, field of view, contrast, edge definition, and artifacts (for example, ghosts and streaks). Under a broad range of conditions, image quality improves with increasing data acquisition time. If the data acquisition time is increased, however, the patient is subjected to a longer scan time, which increases patient discomfort. In some instances, long scan times may actually degrade image quality because of movement of the region of interest during the scan. Short scan times are also necessary for near-real-time measurements, such as used in functional MRI. There is, thus, a trade-off between image quality and scan time.

Images are displayed on physical media; for example, emulsions on film or pixels on a monitor. The normal physical world may be referred to as real space. In one method for producing high-quality images, MR signals are captured in k-space. In some fields of study, k-space is also referred to as spatial-frequency domain. In general terms, data values in real space are then generated by taking the inverse Fourier transform of data values in k-space. In general, MR signals are not measured as a continuous function of position in k-space. They are sampled at discrete k-values. Subject to specific constraints and boundary conditions, image quality generally improves as the density and range of discrete k-space sampling points are increased. Recording a large number of samples, however, has disadvantages. One is the extended scan time discussed above. The other is low temporal resolution.

To reduce data acquisition time, MRI data are often intentionally under-sampled. This will, however, often lead to reduced signal-to-noise ratio (SNR) and to image degradation. Various techniques have been developed to enhance the image quality reconstructed from under-sampled data, but they require extended computational time and high memory usage. Accordingly, novel and improved compressed sensing methods and systems are required which further enhance time-resolved NCE-MRA applications such as generating 4D angiograms.

BRIEF SUMMARY OF THE INVENTION

Aspects of the present invention provide systems and methods to provide non-contrast-enhanced 4D MRA using compressed sensing reconstruction.

In accordance with an aspect of the present invention, a method is provided for reconstructing an image of an object from age data, comprising a processor receiving non-contrast-enhanced magnetic resonance image data of the object containing a first and a second dataset in k-space obtained with a medical imaging device which is acquired in an undersampled manner, the processor generating a sparsified third dataset by subtracting the first from the second dataset in k-space and the processor iteratively minimizing an objective function under a constraint related to the third dataset to reconstruct the image of the object.

In accordance with another aspect of the present invention, a method is provided wherein the objective function includes applying a Karhunen-Loeve Transform (KLT).

In accordance with yet another aspect of the present invention, a method is provided wherein the minimizing of the objective function under the constraint is expressed as arg $\min_f\{\|\phi(f)\|_1$ subject to $\|Af-y\|_2 \le \epsilon\}$, wherein f represents an iterative image, $\phi(f)$ represents the Karhunen-Loeve Transform of f, y represents the third dataset, A represents a Fourier operator that maps the trial image into k-space and $\epsilon$ represents a parameter that accounts for a deviation between a measurement and ideal data.

In accordance with yet another aspect of the present invention, a method is provided wherein the Karhunen-Loeve Transform is applied to data defined in a temporal dimension.

In accordance with yet another aspect of the present invention, a method is provided wherein the processor suppresses an undersampling caused coefficient in a principal component in the KLT transformed data.

In accordance with yet another aspect of the present invention, a method is provided wherein the object is a patient.

In accordance with yet another aspect of the present invention, a method is provided wherein the reconstructed image is an angiogram.

In accordance with yet another aspect of the present invention, a method is provided wherein the angiogram is a 4D angiogram.

In accordance with yet another aspect of the present invention, a method is provided wherein the method is used in diagnosing a vascular disease.

In accordance with a further aspect of the present invention, a system is provided to reconstruct an image of an object from image data, comprising a memory enabled to store data, a processor enabled to execute instruction to perform the steps receiving non-contrast-enhanced magnetic resonance image data of the object containing a first and a second dataset in k-space obtained with a medical imaging device which is acquired in an undersampled manner, generating a sparsified third dataset by subtracting the first from the second dataset in k-space and iteratively minimizing an objective function under a constraint related to the third dataset to reconstruct the image of the object.

In accordance with yet a further aspect of the present invention, a system is provided wherein the objective function includes applying a Karhunen-Loeve Transform (KLT).

In accordance with yet a further aspect of the present invention, a system is provided wherein the minimizing of the objective function under the constraint is expressed as arg $\min_f\{\|\phi(f)\|_1$ subject to $\|Af-y\|_2 \le \epsilon\}$, wherein f represents an iterative image, $\phi(f)$ represents the Karhunen-Loeve Transform of f, y represents the third dataset, A represents a Fourier operator that maps the trial image into k-space and ε represents a parameter that accounts for a deviation between a measurement and ideal data.

In accordance with yet a further aspect of the present invention, a system is provided wherein the Karhunen-Loeve Transform is applied to data defined in a temporal dimension.

In accordance with yet a further aspect of the present invention, a system is provided wherein the processor suppresses an undersampling caused coefficient in a principal component in the KLT transformed data.

In accordance with yet a further aspect of the present invention, a system is provided wherein the object is a patient.

In accordance with yet a further aspect of the present invention, a system is provided wherein the reconstructed image is an angiogram.

In accordance with yet a further aspect of the present invention, a system is provided wherein the angiogram is a 4D angiogram.

In accordance with yet a further aspect of the present invention, a system is provided wherein the system is used in diagnosing a vascular disease.

These and other advantages of the invention will be apparent to those of ordinary skill in the art by reference to the following detailed description and the accompanying drawings.

BRIEF DESCRIPTION OF THE DRAWINGS

FIGS. 4-7 illustrate steps in accordance with one or more aspects of the present invention.

DETAILED DESCRIPTION

Figure 1:
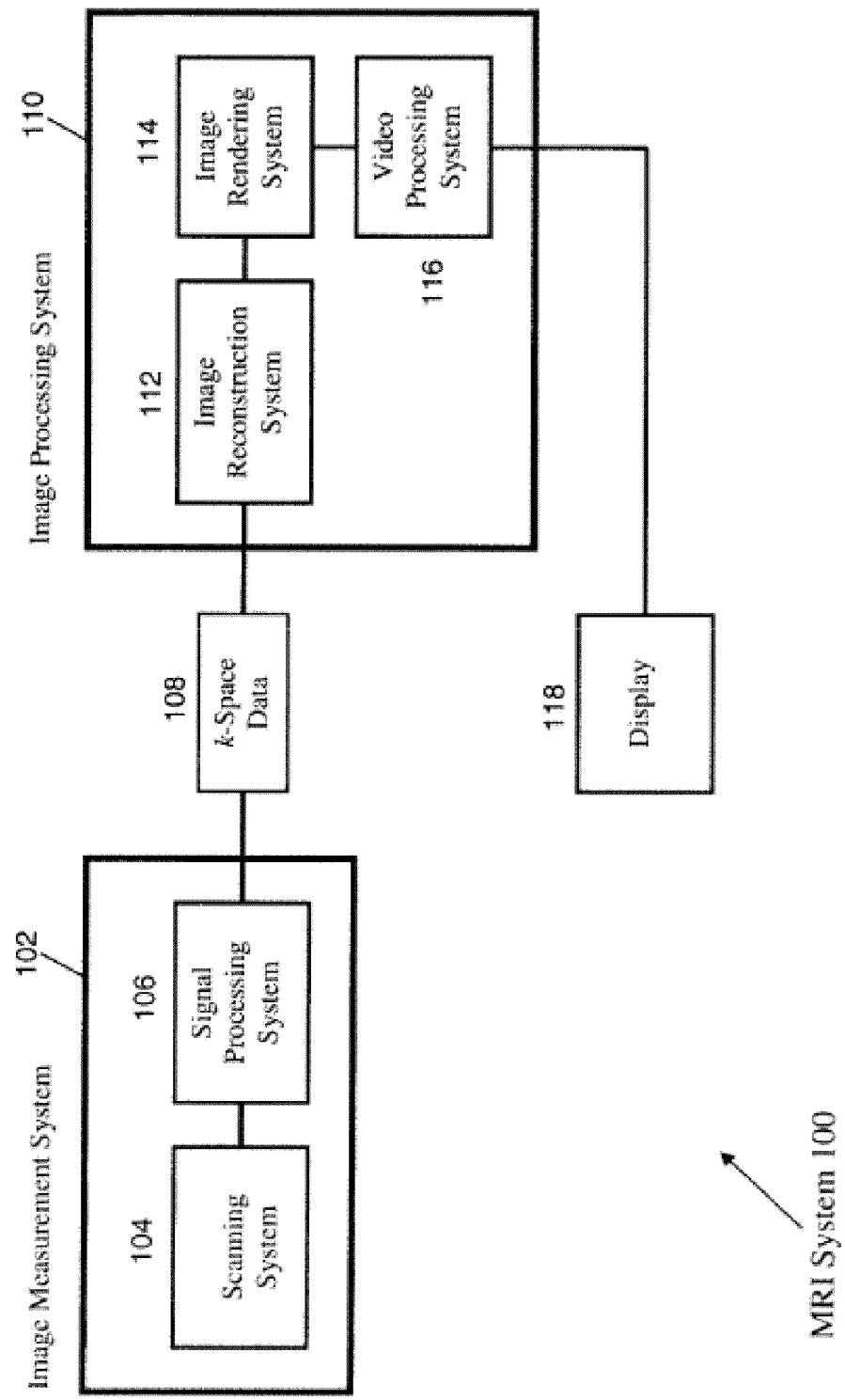
FIG. 1 shows a high-level schematic of an MRI system.

FIG. 1 shows a high-level schematic of the functional architecture of a representative imaging system. In the example shown in FIG. 1, the imaging system is MRI system 100. Embodiments apply to other modalities. MRI system 100 comprises image measurement system 102, image processing system 110, and display 118. Image measurement system 102 may include scanning system 104 and signal processing system 106. Scanning system 104 includes the MRI scanner and associated instrumentation and software. The output of scanning system 104 is radio-frequency (RF) signals which are fed into signal processing system 106. Signal processing system 106 includes hardware and software which converts the RF signals to k-space data 108, which is discussed further below.

The k-space data 108 is then fed into image processing system 10, which may include image reconstruction system 112, image rendering system 114, and video processing system 116. Image reconstruction system 112, further discussed below, transforms k-space data 108 into image-space data, which may be a two-dimensional (2-D) or three-dimensional (3-D) dataset. Herein, image space refers to real space. Herein, image reconstruction refers to the transformation of k-space data to image-space data. The image-space data is then mapped by image rendering system 114 into optical data for further video processing. For example, in a monochrome display, the image-space data may be mapped into the luminance values of pixels. In a color display, image-space data may be mapped into the luminance and false-color values of pixels. Video processing system 116 transforms the output optical data from image rendering system 114 into signals which drive pixels on display 118, which displays the image viewed by a user.

As discussed above, MR signals captured and processed by image measurement system 102 are output as k-space data 108. In general terms, data values in image space are then generated by taking the inverse Fourier transform of k-space data 108. In general, MR signals are not measured as a continuous function of position in k-space. They are sampled at discrete k-values. Subject to specific constraints and boundary conditions, image quality generally improves as the density and range of discrete k-space sample points are increased. For other modalities, k-space is also referred to as spatial-frequency domain.

Coordinates of points in k-space may be specified with respect to a 3-D Cartesian grid, analogous to the common x-y-z Cartesian grid in real space. For MRI analysis, the axes are $k_x$=frequency (also called readout), $k_y$=phase encoding, and $k_z$=slice selection. Alternative coordinate systems, such as polar coordinates, may also be used. The locus of points in k-space along which data is sampled is referred to as the scan trajectory. The simplest trajectories are linear. For example, in a 2-D scan, a value of $k_y$ is held fixed while data is sampled at different values of $k_x$. The linear scans along $k_x$ are then repeated for other fixed values of $k_y$. A disadvantage of linear Cartesian scans is that the scan pattern is relatively slow in the $k_y$ direction.

Acquisition speed may be increased by various techniques. For example, radial or spiral trajectories may be used instead of linear ones. As discussed above, k-space values may be intentionally under-sampled. Images reconstructed from under-sampled data, however, are often degraded by severe artifacts and low SNR. Image quality may be enhanced via iterative MR reconstruction schemes. (See, for example, T-C Chang, et al., MR Image Reconstruction from Sparse Radial Samples Using Bregman Iteration, *Proc.* 14*th. Annual Meeting of ISMRM*, Seattle, Wash., 2006.)

In these schemes, the $L_1$ norm of the sparse representations of the image-space data is minimized, subject to the constraint of k-space data fidelity. A sparse representation of an image is a set of transformed domain coefficients that has much fewer non-zero values than the image of interest. Using the set of coefficients, the image of interest may be constructed, rendered, and displayed.

The problem can be expressed as:

$$\min_{f} \|\varphi(f)\|_1 \text{ subject to } Af = y, \tag{E1}$$

where f is the image-space data arranged in a vector form, φ(.) transforms the image-space data into a sparse representation, y is the measured k-space data arranged in a vector form, and matrix A is a Fourier operator that maps the image-space data into k-space data. Here, $\|\cdot\|_p$ refers to the $L_p$ norm. The image is rendered from f-values which solve the minimization E1. The variable f is also called a trial image, One other way of expressing E1a is:

$$\arg\min_{f} \{\|\phi(f)\|_1 \text{ subject to } \|Af-y\|_2 \leq \epsilon\}, \tag{P1}$$

wherein ε is a parameter that accounts for deviation between measured and ideal data.

The optimization problem of E1 is equivalent to the unconstrained optimization:

$$\min_f \{\psi(f)\}, \quad \text{(E2)}$$

$$\text{with } \psi(f) = \lambda \|\varphi(f)\|_1 + \|Af - y\|_2^2.$$

Here, ψ(f) is a cost functional, λ≥0 is a Lagrange multiplier, and $\|Af-y\|_2^2$ is a data fidelity term. In an embodiment, an iterative non-linear conjugate gradient (CG) method is used to calculate f-values which solve the minimization E2. The solution at iteration k is $$f_{k+1} = f_k + \alpha_k d_k, \quad \text{(E3)}$$

where $$d_{k+1} = -\nabla\psi(f_{k+1}) + \beta_{k+1} d_k \quad \text{(E4)}$$

$$d_0 = -\nabla\psi(f_0) \quad \text{(E5)}$$

$\beta_{k+1}$ is the update direction:

$$\beta_{k+1} = \frac{|\nabla\psi(f_{k+1})|^2}{|\nabla\psi(f_k)|^2}, \quad \text{(E6)}$$

$\alpha_k$ is the step size:

$$\alpha_k = \operatorname*{argmin}_\alpha \psi(f_k + \alpha d_k). \quad \text{(E7)}$$

In E7, a search for $\alpha_k$ may be performed with a backtracking line search method. An example of a backtracking line search method is given by the pseudo-code:
given a descent direction d for the energy functional ψ, γ∈(0, 0.5), δ∈(0, 1);
initializing α:=1;
and while $\psi(f+\alpha d) > \psi(f) + \gamma\alpha\nabla\psi(f)^T d$, setting α:=δα.

Using this formulation, the number of iterations necessary for convergence is high. The cost of each CG iteration is high as well, due to the non-Cartesian nature of the trajectory. The gradient of the data fidelity term in E2 is $A^\dagger(Af-y)$. Fast Fourier transform (FFT) is not directly applicable when applying the Fourier operator A to the image-space data and its adjoint $A^\dagger$ to the k-space data. Conventionally, gridding and inverse gridding methods are used. (See, for example, J. I. Jackson, et al., Selection of a Convolution Function for Fourier Inversion Using Gridding, *IEEE Trans. Med. Imag.*, 10(3), 473-478, 1991 which in incorporated herein by reference.) The gridding accuracy trades off computational speed subject to the choice of gridding kernel. Furthermore, the use of a look-up table in the gridding methods trades off memory usage for computational speed. As a result, using gridding and inverse gridding for the data fidelity term is expensive for 2-D applications, and may be prohibitively high for 3-D applications.

Image reconstruction time may be greatly reduced. In one approach, a k-space weighting, equivalently interpreted as a density compensation function (DCF), is applied to the $L_2$ norm data fidelity term in E2. The minimization problem of E2 is then modified to $$\min_f \{\lambda\|\varphi(f)\|_1 + \|W(Af-y)\|_2^2\}, \quad \text{E8}$$

where W is a diagonal weighting matrix. The modified cost functional is $\lambda\|\varphi(f)\|_1 + \|W(Af-y)\|_2^2$. The matrix $D=W^\dagger W$ can be proportional to the density compensation function, which is well-known in gridding method. The weighting makes the residual nearly perpendicular to the descent direction at each iteration, and thus enables near optimal convergence. The product of the Fourier operator and its adjoint is a block-Toeplitz matrix, and its operation on vectors may be evaluated by FFT. Gridding and inverse gridding time are reduced. The storage of the gridding look-up table is also eliminated.

In another approach, total variation (TV) may be used as $\|\phi(.)\|_1$ due to its convexity, simplicity, and effectiveness for processing medical images. The models represented by E2 and E8 then become total variation regularization models, which are advantageous in a wide variety of restoration problems, such as denoising, deblurring, blind deconvolution, and in-painting. TV norm is effective in reducing oscillations without penalizing discontinuities. Thus, it may mitigate streaking artifacts while preserving edge definition. By selecting different values for λ, a user may select the level of detail desired in the reconstructed image. The Lagrange multiplier λ is usually chosen relatively small to emphasize the data fidelity term and avoid artifacts introduced by over-penalizing the TV norm. Examples of artifacts include staircasing (blocking) and degradation of contrast, geometry, and texture. The convergence of the algorithm is, therefore, largely decided by the data fidelity term.

Other approaches have been disclosed in U.S. Pat. No. 7,864,999 issued on Jan. 4, 2011 to Chang et al. and U.S. Pat. No. 7,903,858 issued on Mar. 8, 2011 to Chang et al. which are both incorporated herein by reference.

Among a few conceptually equivalent formulations of compressed sensing, the constraint optimization herein is articulated as:

$$\arg\min_f \{\|\phi(f)\|_1 \text{ subject to } \|Af-y\|_2 \leq \epsilon\}. \quad \text{E9}$$

Herein in E9, f is a trial image; φ(f) transforms f into a sparse representation; y is the measured k-space data; A is a Fourier operator that maps the image into k-space; and ε is a parameter that accounts for deviation between the measurement and ideal data. Eq. E9 is the conventional CS formulation that solely relies on the sparsity assumption. The image reconstruction as represented by E9 is an iterative reconstruction. It starts out with an initial trial image f, which will be updated by performing iterative steps. Another and equivalent term for "trial image" herein is "iterative image." An image or image data represented by f, g, g̃ or y is represented and processed in vector or matrix form. Use of these symbols herein thus inherently represent vectors which may be multi-dimensional vectors.

In recent years, non-contrast magnetic resonance angiography (NCE MRA) has been an emerging tool in the diagnosis of degenerative vascular disease such as disclosed in M. Miyazaki and V. S. Lee, Nonenhanced MR angiography, Radiology 248(1):20-43 (2008). In this context, a novel time-resolved data acquisition method was proposed in X. Bi et al. Non-Contrast-Enhanced Four-Dimensional (4D) Intracranial MR Angiography: A Feasibility Study Magnetic Resonance in Medicine 63:835-841 (2010), which is incorporated herein by reference. This technique uses two ECG-triggered CINE-like b-SSFP acquisitions of multiple 3D phases: One after selective and another one after non-selective inversion. With a subtraction of the two datasets, the background signal can be eliminated, and the difference between the signals of differently labeled inflowing blood yields time-resolved vascular information.

Desired improvements include a reduction of the total scan time to reduce the impact of unintentional motion as well as an increase of the spatial and/or temporal resolution. Thus, the compressed sensing (CS) technique, which aims at reconstructing high quality signal from largely undersampled acquisitions, is a natural fit to further enhance time-resolved NCE-MRA applications. Undersampling is a well known aspect of compressed sensing and is the detection of a specimen not fully representative of a whole.

Methods

Given the assumption that the image to be reconstructed is sparse or can be sparsified by some transformations, compressed sensing theory shows that the sparsest solution to the L1-L2 minimization problem of E9 recovers the true image with high probability.

Because 4D NCE-MRA acquires two repetitions with the same anatomical location but different contrast mechanism for the vessels, after subtraction between the two repetitions, the resulting 3D image sequence would be sparse. Therefore, the reconstruction is performed on the signal subtracted sequence to better satisfy the requirement of the compressed sensing theory. This is opposed to the conventional procedure which reconstructs the two 4D data sets and then performs subtraction.

As an aspect of the present invention and in application of Cartesian 4D NCE-MRA, the Karhunen-Loeve transform (KLT) is applied in the temporal dimension to obtain the sparse representation; A is simply a subsampled Fourier matrix; and E9 is solved by NESTA with the reweighted L1 scheme as is known in the art and described in as described in Becker et al., NESTA: A Fast and Accurate First-order Method for Sparse Recovery, SIAM J. on Imaging Sciences, 2011 page 1-39.

The KLT first finds the principal components which are the eigen-vectors of the signal covariance matrix, and then projects the signal onto these vectors to obtain decomposition coefficients. The major principal axis corresponds to the direction that the coefficients along this direction has the largest variance. Therefore in the present case, most sparse bright vessels in the images are represented (after the KLT) as a few large coefficients in the major principal component; and most artifacts and noise will result in smaller coefficients distributed in those components other than the major one. These artifacts and noise are then suppressed while the objective function is minimized; and the true structures are preserved while the constraint is satisfied in E9.

Results

With the acquisition scheme described in X. Bi et al. Non-Contrast-Enhanced Four-Dimensional (4D) Intracranial MR Angiography: A Feasibility Study Magnetic Resonance in Medicine 63:835-841 (2010), 4D NCE-MRA data were acquired in healthy volunteers on a 3.0T clinical MR scanner (Magnetom Trio a Tim System, Siemens AG). The data size was 112×84×30×13×2×4, where the numbers denote, in order, height, width, partition, phase, repetition (i.e. two different labelings) and coil channel number.

In the reconstruction procedure which is an aspect of the present invention, first the two repetitions in k-space (which are called a first and a second dataset in k-space) are subtracted to obtain a "vessel-only" representation. For demonstrative reasons the reconstruction was restricted to two spatial dimension and the temporal dimension at a time and applied it separately for each partition and each channel. This means that the dimension of f as in E9 was 112×84×13; and a total of 30×4 reconstructions needed to be performed. The 4 independent receiver channels were afterwards combined as the sum of squares. To model random sampling as suggested by the compressed sensing (CS) theory, a fully sampled data (112 phase encoding lines) was started for each frame, and 14 lines (8× acceleration) were selected for reconstruction.

Specifically, 7 out of the 14 lines are chosen to fill the k-space center, while the remaining 7 were uniformly and randomly distributed in remaining k-space.

The experimental results, which were obtained by maximum intensity projection (MIP) to the transverse plane for the 10th phase, are shown in FIG. 2 for the different reconstruction approaches.

Figure 2A:
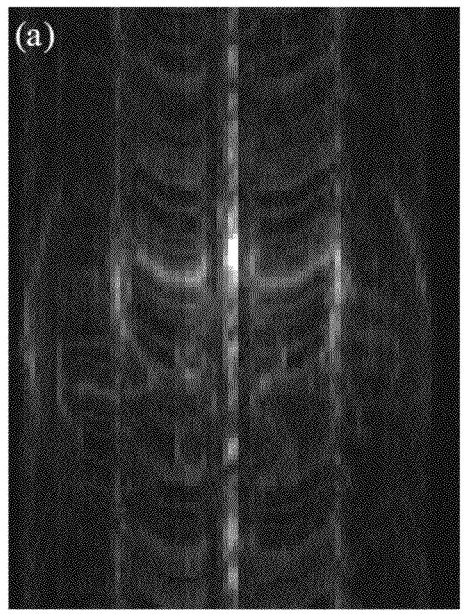
FIG. 2 illustrates reconstructed images including at least one generated in accordance with an aspect of the present invention.
Figure 2B:
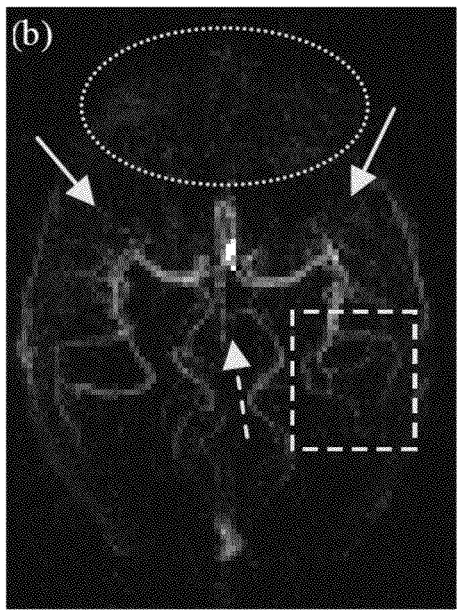
Figure 2C:
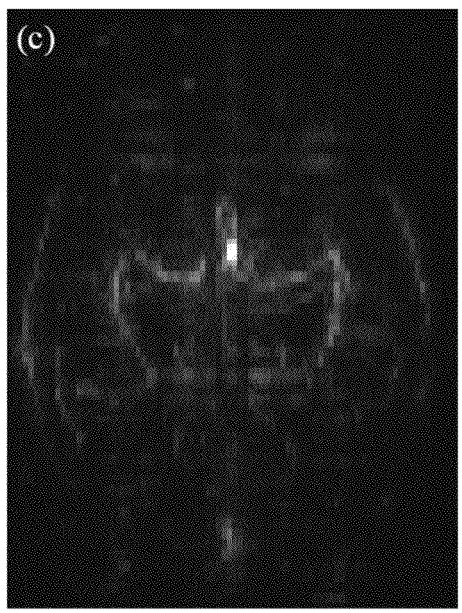
Figure 2D:
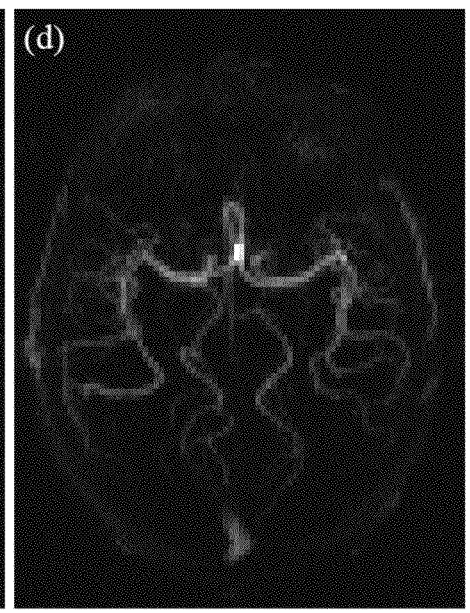

FIG. 2 shows MIP images showing reconstruction by in FIG. 2(a) the Fourier transform with zero-filling, in FIG. 2(b) no sparsifying transform in E9, i.e., φ is the identity mapping, in FIG. 2(c) setting φ to be the Daubechies-8 wavelet spatial transform, in FIG. 2(d) setting φ to be the Karhunen-Loeve Transform (KLT) which is applied in the temporal dimension, and (e) the Fourier transform with the fully sampled data, i.e., the ground truth. These methods are also referred to as (a), (b), (c), (d), and (e).

Figure 2E:
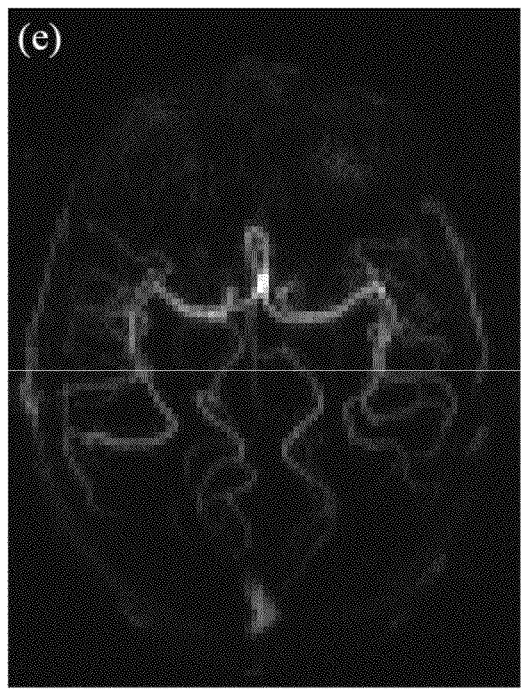

FIG. 2(a) illustrates the severe aliasing artifacts when we directly applied the Fourier transform to the undersampled data with zero-filling. Comparing with the ground truth in FIG. 2(e), FIG. 2(b) has higher noise level, missing details, lower quality vessels, and residual aliasing artifacts, as indicated by, respectively, the dashed ellipse, the solid arrows, the dashed square, and the dashed arrow. It is clear that in FIG. 2(c) the residual aliasing artifacts are still dominant and many details are missing. FIG. 2(d) is a result of the method that is an aspect of the present invention and that achieves comparable visual image quality as that of the ground truth, which is shown in FIG. 2(e).

Quantitatively, the mean squared error (MSE) was computed between the energy-normalized reconstructed 4D volume (size 112×84×30×13) and the ground truth, and divided by the energy of the ground truth to obtain the relative MSE (rMSE). The rMSE for the methods (a)~(d) are, respectively, 3.47, 0.72, 1.66, 0.47, which correspond well with the visual quality and also justify the use of the KLT. Note that the rMSE only gives a relative quality measure because the ground truth is fully sampled so that its energy is essentially different from the undersampled reconstruction.

The technique introduced in X. Bi et al. Non-Contrast-Enhanced Four-Dimensional (4D) Intracranial MR Angiography: A Feasibility Study Magnetic Resonance in Medicine 63:835-841 (2010) represents a promising approach for time-resolved 4D NCE-MRA. It has been demonstrated herein that further improvements in spatial/temporal resolution or a reduction in acquisition time are feasible by CS reconstruction from undersampled acquisitions. By subtracting the two differently spin-labeled datasets in k-space, it is possible to work on images with vascular structures only, i.e. images that are sparse in the image domain. To further sparsify the data and facilitate CS framework, the KLT was applied in the temporal dimension. Finally, a state-of-the-art solver (the herein mentioned NESTA method) was adapted for the L1-L2 minimization problem. The results generated with the a method that is provided as an aspect of the present invention show that results comparable to the ground truth can be achieved at 8-fold acceleration.

A natural extension of current work is to add algorithms that exploit the spatial sensitivity information of the multiple coil elements and to perform a true 4D reconstruction in order to achieve even higher acceleration rates.

Figure 3:
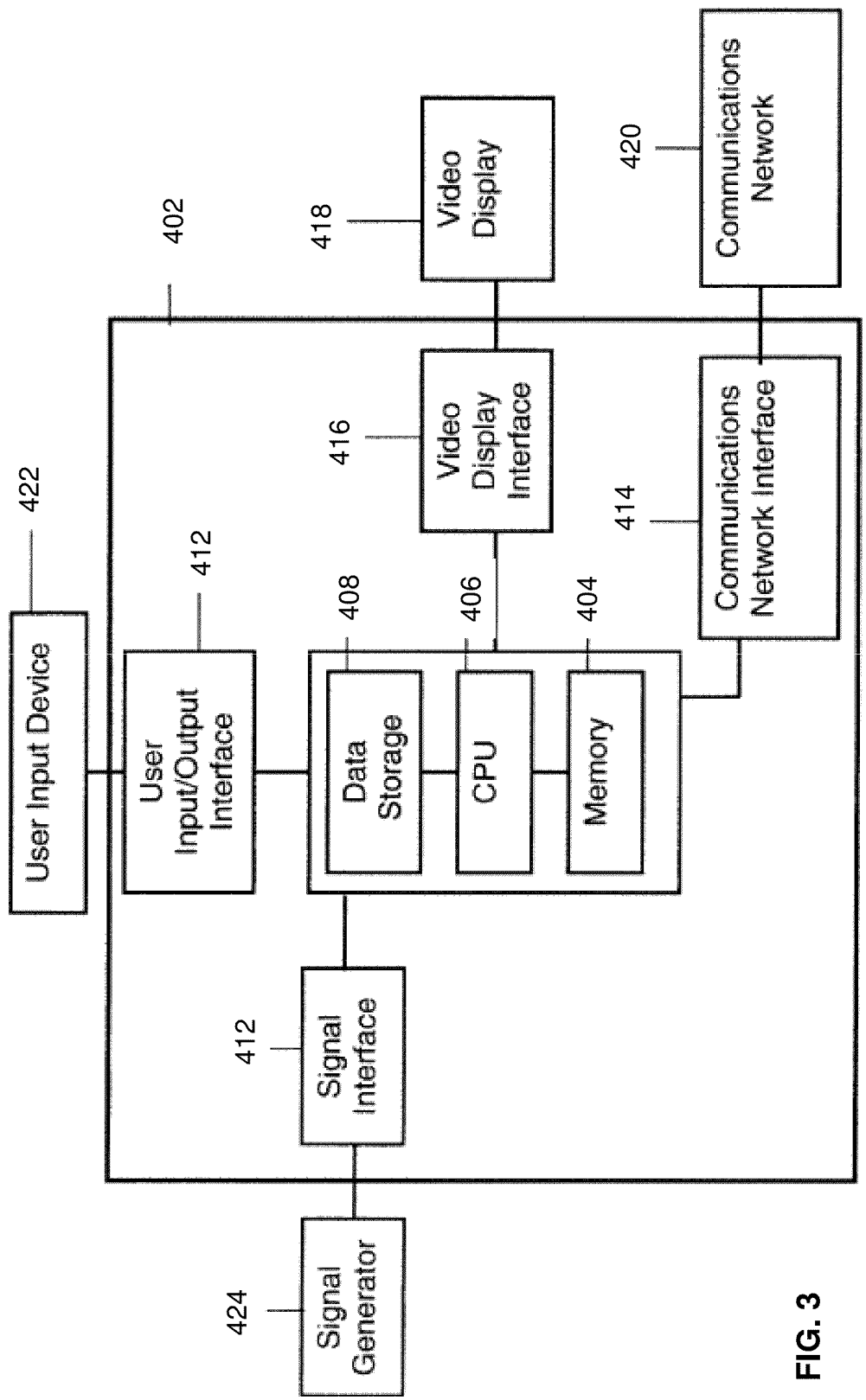
FIG. 3 illustrates a high-level schematic of a computer for performing image reconstruction.

One embodiment of an image processing system 110 (FIG. 1) may be implemented using a computer. As shown in FIG. 3, computer 402 may be any type of well-known computer comprising a central processing unit (CPU) 406, memory 404, data storage 408, and user input/output interface 410. Data storage 408 may comprise a hard drive or non-volatile memory. User input/output interface 410 may comprise a connection to a user input device 422, such as a keyboard or mouse. As is well known, a computer operates under control of computer software which defines the overall operation of the computer and applications. CPU 406 controls the overall operation of the computer and applications by executing computer program instructions which define the overall operation and applications. The computer program instructions may be stored in data storage 408 and loaded into memory 404 when execution of the program instructions is desired. Computer 402 may further comprise a signal interface 412 and a video display interface 416. Signal interface 412 may transform incoming signals, such as from measurement system 102 (FIG. 1), to signals capable of being processed by CPU 306. Video display interface 416 may transform signals from CPU 406 to signals which may drive video display 418. Computer 402 may further comprise one or more network interfaces. For example, communications network interface 414 may comprise a connection to an Internet Protocol (IP) communications network 420. Computers are well known in the art and will not be described in detail herein.

Figure 5:
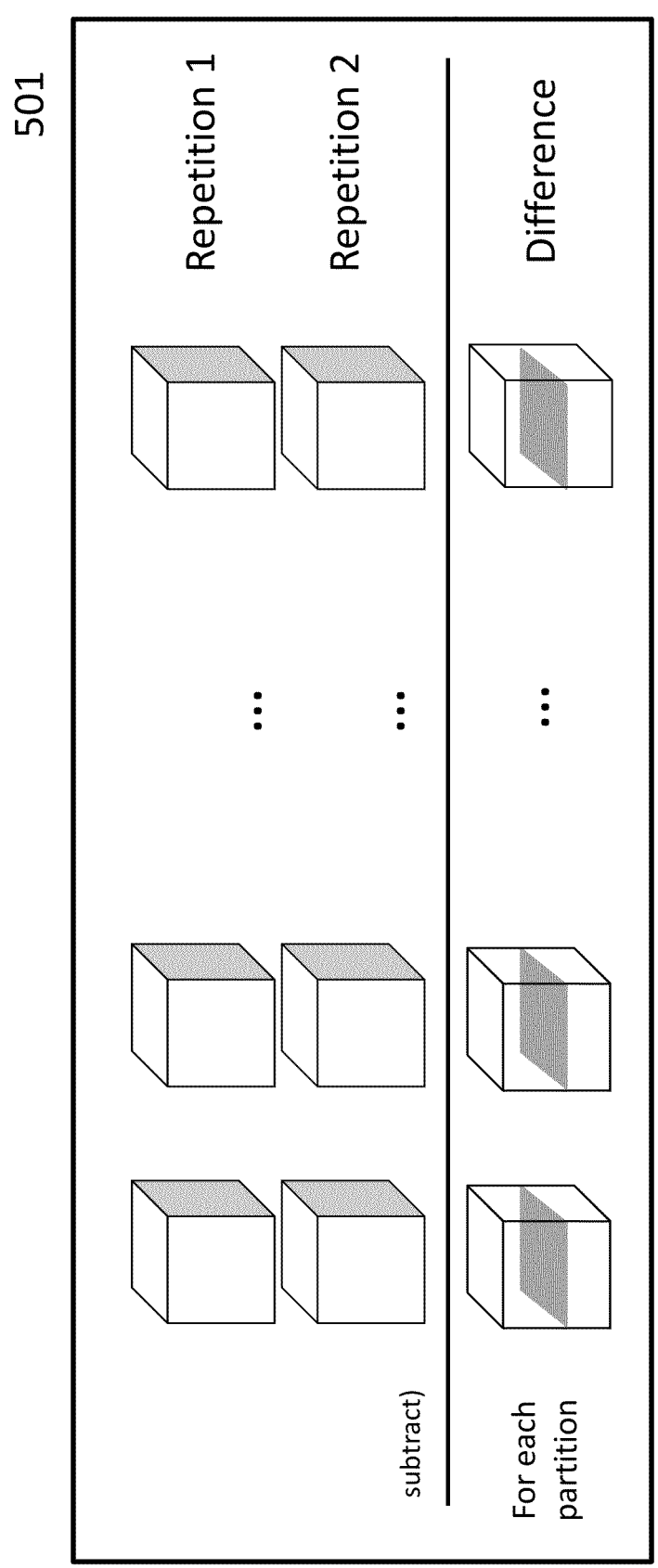
Figure 6:
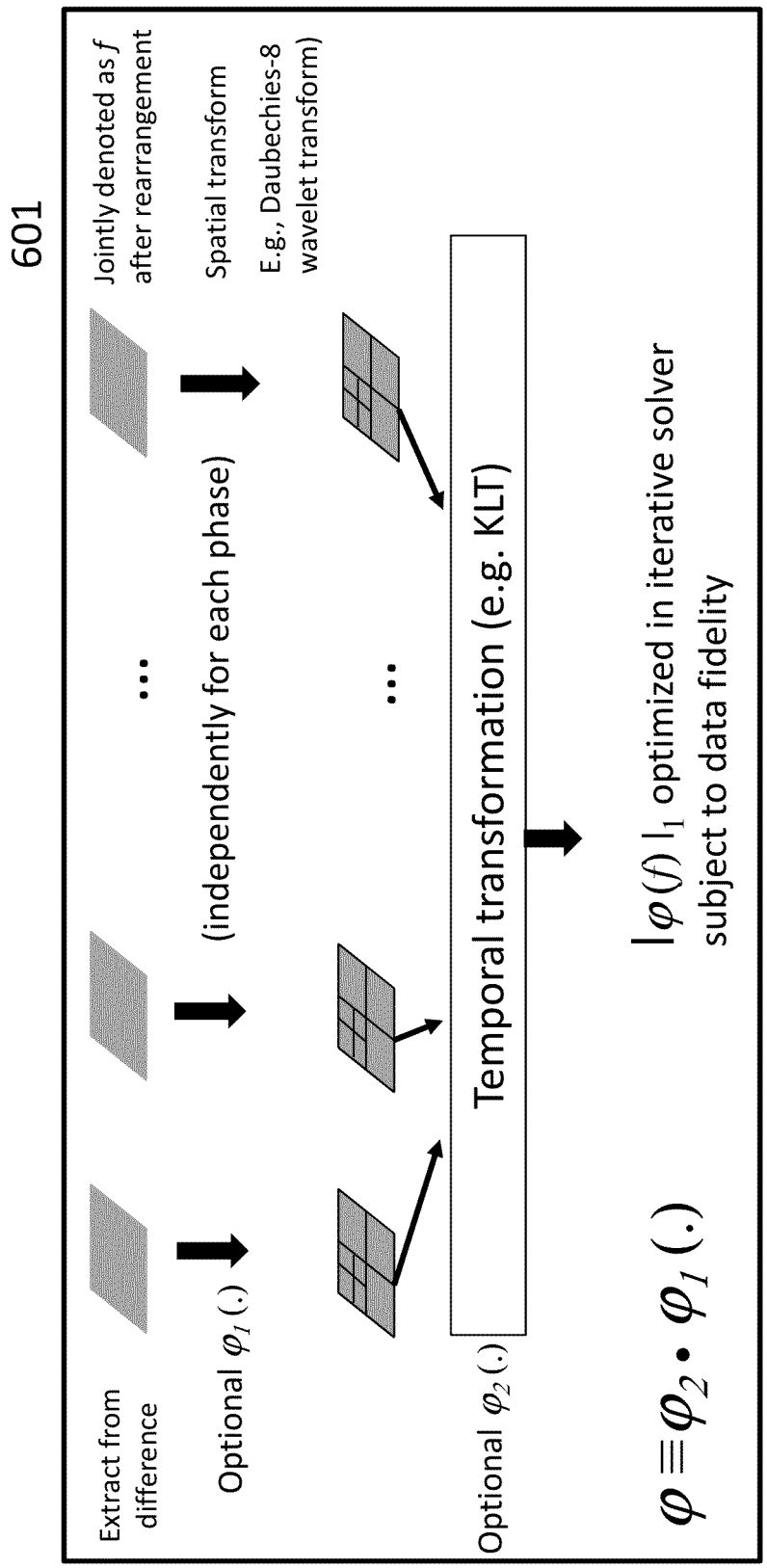

Steps performed in accordance with one or more aspects of the present invention are illustrated in FIGS. 4-7. FIG. 4 block 401 illustrates the iterative steps of minimizing an objective function under a constraint. Block 501 in FIG. 5 illustrates the subtraction of the data acquired in two repetitions. Block 601 in FIG. 6 illustrates data extraction from the difference set and performing (optionally) a Karhunen Loeve Transformation followed by an iterative solver to reconstruct an image from the difference data set. Block 701 in FIG. 7 illustrates the (optional) step of 601 of performing the Karhunen-Loeve Transform. It is again noted that in one embodiment of the present invention the difference set by itself is considered to represent sufficiently sparsified data so that a further sparsifying transformation is not performed. The iterative solver is operated on difference data.

In another embodiment of the present invention the difference data set is transformed, for instance by a KLT. The iterative solver is operated on difference data that has been transformed, for instance by a KLT.

In one embodiment of the present invention, the acquired data is acquired in a random or pseudo-random or a non-uniform manner in the phase encoding direction. In a further embodiment of the present invention, data acquisition can be performed using uniform or square-law or other power-low distributed spacing but with offsets or shifts between different temporal phases and reconstructed in accordance with an aspect of the present invention.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for reconstructing an image of an object from image data, comprising:

a processor receiving non-contrast-enhanced magnetic resonance image data of the object containing a first and a second dataset in k-space obtained with a medical imaging device which are acquired in an undersampled manner, wherein the first and second dataset in k-space are steady-state free precession (SSFP) repetition acquisitions of one phase of multiple phases in a cine angiography;

the processor generating a sparsified third dataset prior to image reconstruction by creating a difference set in k-space by subtracting the first from the second dataset in k-space and by applying a Karhunen-Loeve Transform (KLT) over a temporal dimension of an inverse Fourier Transform of the difference set; and the processor iteratively minimizing an objective function under a constraint related to the sparsified third dataset to reconstruct the image of the object, wherein one or more artifacts due to the acquisition in the undersampled manner are suppressed.

2. The method of claim 1, wherein the minimizing of the objective function under the constraint is expressed as $$\arg\min_f \{\|\phi(f)\|_1 \text{ subject to } \|Af-y\|_2 \le \epsilon\}, \text{ wherein}$$

f represents an iterative image;

$\phi(f)$ represents the Karhunen-Loeve Transform of f;

y represents the sparsified third dataset;

A represents a Fourier operator that maps the iterative image into k-space; and $\epsilon$ represents a parameter that accounts for a deviation between a measurement and ideal data.

3. The method of claim 1, wherein the object is a patient.

4. The method of claim 1, wherein the reconstructed image is an angiogram.

5. The method of claim 4, wherein the angiogram is a 4D angiogram.

6. The method of claim 1, wherein the method is used in diagnosing a vascular disease.

7. The method of claim 1, wherein the suppression of the one or more artifacts introduced by the undersampled acquisition, which is expressed as a relative mean squared error between an energy-normalized reconstructed 4D volume using the steps of claim 1 and a fully sampled ground truth, compared to a relative mean squared error between an energy-normalized reconstructed 4D volume that does not apply KLT on the undersampled acquisition and a fully sampled ground truth, is at least 35% lower.

8. A system to reconstruct an image of an object from image data, comprising:

a memory enabled to store data;

a processor enabled to execute instructions to perform the steps:

receiving non-contrast-enhanced magnetic resonance image data of the object containing a first and a second dataset in k-space obtained with a medical imaging device which are acquired in an undersampled manner, wherein the first and second dataset in k-space are steady-state free precession (SSFP) repetition acquisitions of one phase of multiple phases in a cine angiography;

generating a sparsified third dataset prior to image reconstruction by creating a difference set in k-space by subtracting the first from the second dataset in k-space and by applying a Karhunen-Loeve Transform (KLT) over a temporal dimension of an inverse Fourier Transform of the difference set; and iteratively minimizing an objective function under a constraint related to the sparsified third dataset to reconstruct the image of the object, wherein one or more artifacts due to the acquisition in the undersampled manner are suppressed.

9. The system of claim 8, wherein the minimizing of the objective function under the constraint is expressed as $$\arg\min_f \{\|\phi(f)\|_1 \text{ subject to } \|Af-y\|_2 \leq \epsilon\}, \text{ wherein}$$

f represents an iterative image;

$\phi(f)$ represents a the Karhunen-Loeve Transform of f;

y represents the sparsified third dataset;

A represents a Fourier operator that maps the iterative image into k-space; and $\epsilon$ represents a parameter that accounts for a deviation between a measurement and ideal data.

10. The system of claim 8, wherein the object is a patient.

11. The system of claim 8, wherein the reconstructed image is an angiogram.

12. The system of claim 11, wherein the angiogram is a 4D angiogram.

13. The system of claim 8, wherein the system is used in diagnosing a vascular disease.

14. The system of claim 8, wherein the suppression of the one or more artifacts introduced by the undersampled acquisition, which is expressed as a relative mean squared error between an energy-normalized reconstructed 4D volume using the steps of claim 8 and a fully sampled ground truth, compared to a relative mean squared error between an energy-normalized reconstructed 4D volume that does not apply KLT on the undersampled acquisition and a fully sampled ground truth, is at least 35% lower.

* * * * *